US011541158B2

(12) United States Patent
Turner et al.

(10) Patent No.: US 11,541,158 B2
(45) Date of Patent: Jan. 3, 2023

(54) OXYGENATION SYSTEM

(71) Applicant: Spectrum Medical Ltd., Gloucestershire (GB)

(72) Inventors: Stephen Turner, Gloucestershire (GB); Benjamin David Garbutt, Gloucestershire (GB)

(73) Assignee: Spectrum Medical Ltd., Gloucester (GB)

( * ) Notice: Subject to any disclaimer, the term of this patent is extended or adjusted under 35 U.S.C. 154(b) by 1253 days.

(21) Appl. No.: 15/994,315

(22) Filed: May 31, 2018

(65) Prior Publication Data

US 2018/0344918 A1 Dec. 6, 2018

(30) Foreign Application Priority Data

Jun. 2, 2017 (GB) ...................................... 1708810

(51) Int. Cl.
*A61M 1/36* (2006.01)
*A61M 1/16* (2006.01)
*A61G 10/02* (2006.01)
*A61M 16/18* (2006.01)
*B01D 19/00* (2006.01)

(52) U.S. Cl.
CPC ......... *A61M 1/3627* (2013.01); *A61G 10/023* (2013.01); *A61M 1/1698* (2013.01); *A61M 16/18* (2013.01); *B01D 19/0031* (2013.01); *B01D 19/0042* (2013.01); *B01D 19/0063* (2013.01); *A61M 2205/3331* (2013.01); *A61M 2205/3334* (2013.01); *A61M 2205/3341* (2013.01)

(58) Field of Classification Search
None
See application file for complete search history.

(56) References Cited

U.S. PATENT DOCUMENTS 5,158,534 A * 10/1992 Berry .................. A61M 1/1698
604/6.14
2016/0220746 A1 8/2016 Gipson
2020/0188568 A1* 6/2020 Gipson ............... A61M 1/1698

FOREIGN PATENT DOCUMENTS

| DE | 3207174 A1 | 9/1983 |
| GB | 2533027 A | 6/2016 |
| WO | WO 2013/128375 A1 | 9/2013 |
| WO | WO 2016/087859 A1 | 6/2016 |
| WO | WO 2018/026671 A1 | 2/2018 |

OTHER PUBLICATIONS

United Kingdom Intellectual Property Office, Combined Search and Examination report under Section 17 and 18(3)—Application No. GB1708810.5, dated Nov. 27, 2017, 7 pages.
European Patent Office, Extended Search Report for Application No. EP 18175233.8, dated Oct. 15, 2018, 9 pages.

* cited by examiner

*Primary Examiner* — Jason M Greene
(74) *Attorney, Agent, or Firm* — Sunstein LLP

(57) ABSTRACT

An exhaust gas flow control system for an oxygenator of an extracorporeal ventilation system connected to an oxygenation gas supply line and to an exhaust line for removal of exhaust gas comprises a flow control path, a pressure control path, an exhaust flow regulator responsive to the controller, and an exhaust gas pressure regulator responsive to a controller configured to maintain a pre-determined pressure level in the exhaust line. This provides a better degree of control over the pressure across the oxygenator from oxygenation gas inlet to exhaust.

17 Claims, 3 Drawing Sheets

OXYGENATION SYSTEM

PRIORITY

This patent application claims priority from UK Patent Application No. GB 1708810.5, filed Jun. 2, 2017, and entitled "Oxygenation System", and naming Stephen Turner and Benjamin David Garbutt as inventors, the disclosure of which is incorporated herein, in its entirety, by reference.

TECHNICAL FIELD

The present invention relates to an oxygenation system and to a method for extracorporeal blood oxygenation and carbon dioxide control. In particular, the present invention relates to controlling the exhaust gas flow of an oxygenation system, specifically a hypobaric oxygenation system as may be used to reduce the formation of gaseous microemboli bubbles (GME).

BACKGROUND ART

Extracorporeal perfusion is a process in which blood from a patient is circulated outside the patient's body, to be re-oxygenated and to have its carbon-dioxide levels adjusted, to be returned to the patient. More specifically, venous (oxygen-reduced) blood which has been removed from a patient via an incoming line, or venous line, ("incoming" being blood from a patient entering the extracorporeal perfusion system) is oxygenated by exposure to an oxygenation gas in an oxygenator for supply via an outgoing line, or arterial line, back to the patient as arterial blood.

Extracorporeal perfusion is used to substitute heart and lung functionality during a medical procedure, such as open heart surgery or lung treatment. Extracorporeally, blood is brought into a condition for subsequent return to the patient. Blood conditioning includes setting an appropriate temperature, flow rate, line pressure, and mixing with agents such as anti-coagulants. The oxygen content of the blood is increased in an oxygenator, where also the blood carbon dioxide content is adjusted. In the oxygenator, blood is exposed to an oxygenation gas via an interface through which oxygen is permitted to diffuse into the blood to be taken up by the blood. After blood has left the oxygenator, there is usually no further possibility to control the oxygen content before the blood is administered to a patient. To provide an illustration of the flow rates involved, in adult patients, blood is circulated at a typical flow rate in the region of 5 litres per minute (lpm). For this and other reasons, many parameters must be controlled in a short time to ensure that the blood leaving the oxygenator is appropriately oxygenated and carbon dioxide levels are appropriate.

International patent application PCT/GB2015/053694 by the present applicant, published as WO2016/087859, the contents of which are incorporated by reference, discloses an oxygenation system for extracorporeal ventilation comprising a flow control arrangement for controlling the flow rate of an exhaust gas withdrawn from an oxygenator relative to an oxygenation gas supplied to the oxygenator.

WO2016/087859 also discloses a blender for preparing an oxygenation gas to be supplied to an oxygenator. The oxygenator is part of a ventilation system that comprises a flow controller to control the oxygenation gas flow rate to the oxygenator and that is capable of setting the oxygen content with high accuracy at low flow rates.

The flow control and blender arrangements disclosed in WO2016/087859 can be used to maintain low flow rates of an oxygenation gas while also permitting a high degree of blending accuracy and while permitting the exhaust gas to be withdrawn at an appropriate flow rate that is low, yet higher than the oxygenation gas supply.

As stated in WO2016/087859, oxygenation is performed at atmospheric pressure, although vacuum, or a low-pressure source, may be employed to assist with a controlled exhaust gas removal at low flow rates. To ensure atmospheric pressure is maintained, typical oxygenators comprise fail-safe vents in the form of openings in the oxygenator housing to permit gas passage between the oxygenator exhaust chamber and the atmosphere, to prevent over-pressurisation in the oxygenator exhaust chamber.

Oxygenation gas, or so-called "sweep" gas, is usually provided to an oxygenator at a flow rate in the region of 1 to 15 litres per minute (lpm), although rates may sometimes be higher. Exhaust gas is removed from the oxygenator at similar flow rates. In this context, flow rates are considered to be low when in the region of less than 1 lpm to about 4 lpm.

The present invention is concerned with providing additional options for exhaust gas flow control during extracorporeal perfusion.

SUMMARY OF THE EMBODIMENTS

In accordance with a first aspect of the present invention, there is provided an exhaust gas flow control system as defined in claim 1.

The exhaust gas flow control system is provided for an oxygenator of an extracorporeal ventilation system, wherein the oxygenator is of a type connected to an oxygenation gas supply line and an exhaust line through which exhaust gas may be removed.

The exhaust gas flow control system comprises an exhaust pressure regulator responsive to a controller configured to maintain a pre-determined pressure level in the exhaust line.

By 'configured to maintain a pressure level', it is meant that the configuration is capable of modulating the exhaust line pressure, i.e., in response to temporary fluctuations such that the pressure level can be kept at a set point.

A configuration permitting a pre-determined pressure level to be maintained in the exhaust line allows a better degree of control of the pressure environment at the exhaust side of the oxygenator. This facilitates monitoring of gas flow conditions across the oxygenator and may facilitate the evaluation of data. This is helpful in establishing a pre-determined pressure profile from the inlet to the exhaust of the oxygenator.

It will be understood that the oxygenator is located upstream of the exhaust line. Where the present specification refers to an exhaust line pressure, this is for the purpose of providing a pre-determined pressure level at the exhaust side of an oxygenator; the oxygenator being positioned upstream of the exhaust line.

To provide a more precise description, a certain minimum pressure gradient is required from the inlet to the exhaust of an oxygenator to the extent a pressure gradient is required to induce gas flow, but above a minimum flow-inducing pressure gradient, for practical purposes, a pressure gradient from inlet to exhaust is undesirable. For simplicity, it is therefore considered that oxygenators should have "no" inlet-to-exhaust pressure gradient, ie that the pressure profile in the gas phase from inlet to exhaust is for practical purposes constant.

The inlet-to-exhaust pressure profile is to be distinguished from the gas-to-blood pressure gradient across the gas-blood interface of the oxygenator, where a gradient is expected and required to control the exchange of oxygen and carbon dioxide between oxygenation gas and blood.

A configuration allowing the exhaust line pressure to be maintained at a pre-determined level facilitates the provision of a known pressure profile from the inlet to the exhaust of an oxygenator.

The exhaust gas flow control system comprises an exhaust flow regulator responsive to the controller. In embodiments, the controller is configured to maintain a pre-determined flow rate of the exhaust gas passing through the exhaust flow regulator.

The controller may comprise multiple control units. As such, the exhaust flow regulator may be controlled by a first control unit and the exhaust gas pressure regulator may be controlled by a second control unit. The exhaust flow regulator and the exhaust gas pressure regulator may be controlled by the same controller.

The exhaust flow controller is capable of controlling the exhaust flow rate at levels in the region of several few litres per minute (lpm), ranging from in the region of 1 to 15 lpm, although may occasionally be lower or higher than these values.

Compared to providing a single regulator to regulate both flow rate and pressure, the provision of both a flow controller and pressure regulator facilitates achieving a higher degree of accuracy when it is desired to control both the flow rate and a pressure level at a pre-determined level.

This also allows the same level of pressure regulation accuracy to be used at different flow rates, as the flow controller set point may be adjusted to correspond to a particular lower or higher flow rate, to allow the pressure regulator to operate practically independently of a change in flow rate.

The flow controller functionality and the pressure regulator functionality may be provided by the same type of device, e.g., by the same type of control valve. The flow controller may be a different type of device than the pressure regulator.

The exhaust gas flow control system comprises a flow control path controlled by the flow controller and a pressure control path controlled by the pressure regulator.

The provision of a separate flow path for exhaust gas flow control and a separate flow path for pressure regulation increases the accuracy of the flow rate and of the pressure levels.

The proportion of exhaust gas channelled via the flow control path and the pressure control path may be chosen according to the capacity of the exhaust flow regulator and the exhaust gas pressure regulator. For instance, this allows a first flow path to be used in which a portion exhaust gas is transported with a higher flow rate and a second flow path in which another portion of the exhaust is transported with a lower flow rate.

A practical benefit of this arrangement is that a larger range of models of pressure regulators and flow controllers can be used for the design of an exhaust gas flow control system.

In some embodiments, the exhaust gas flow control system comprises a supply line pressure regulator upstream of the oxygenator. Optionally, the exhaust gas pressure regulator is configured to maintain a sub-atmospheric pressure level in the exhaust line.

It will be understood that the expression "upstream of the oxygenator" refers to the oxygenation gas supply line. A pressure regulator in the oxygenation gas supply line allows a different pressure level to be provided downstream of the pressure regulator than upstream of the pressure regulator.

Particularly for sub-atmospheric oxygenation, such an arrangement means that it is not necessary for the entire supply gas line to be operating at sub-atmospheric pressures. The supply gas can be provided at atmospheric pressures to the point of the pressure regulator. This facilitates the handling (preparation and mixing) of the supply gas, which can be performed at atmospheric pressure, before the supply gas pressure is regulated, eg to a sub-atmospheric pressure.

For ventilation under anaesthesia influence, it is an option to supply anaesthesia via the oxygenation gas supply, using an anaesthesia vaporiser. Existing anaesthesia vaporisers are designed for use at atmospheric pressures. At sub-atmospheric pressures, anaesthetic agent would be released at much faster rates than intended.

A supply line pressure regulator downstream of the anaesthesia vaporiser allows anaesthesia release mechanisms to be used that are designed for use at atmospheric pressure. This facilitates integration of legacy anaesthesia release systems.

If the oxygenator is a closed system, the pressure inside an oxygenator from a supply gas inlet to an exhaust gas outlet may be maintained below atmospheric pressure. By "closed system", it is meant that the gas pathways between the oxygenator inlet and the oxygenator exhaust are pressure-isolated from the atmosphere outside of the oxygenator. A closed system allows sub-atmospheric pressure levels in the oxygenator while the outside of the oxygenator can be expected to be at ambient pressure.

By providing a pressure regulator that can operate at sub-atmospheric pressures, the exhaust gas flow control system is suitable for hypobaric oxygenation. The pressure regulator may be able to operate at both atmospheric and sub-atmospheric pressures. The exhaust gas flow control system may be suitable for both conventional (atmospheric) oxygenation and for hypobaric (sub-atmospheric) oxygenation.

As an example of a system suitable for hypobaric oxygenation, Great British patent application GB1705556.7 by the present applicant discloses a pressure-isolation device and method that pressure-isolates an oxygenator exhaust chamber from the outside environment in order to allow oxygenation to be performed in closed-system conditions and, thus, at sub-atmospheric pressures. The pressure isolation device described in GB1705556.7 provides a fail-safe mechanism against over-pressurisation of the exhaust gas chamber.

For instance, hypobaric oxygenation may be performed at sub-atmospheric pressure, e.g. at around half atmospheric pressure (e.g., 500 mbar below atmospheric pressure). The present arrangement allows the exhaust gas flow rate to be maintained at a pre-determined level within small tolerances at sub-atmospheric pressures, while also maintaining the sub-atmospheric pressure level within small tolerances.

In some embodiments, the exhaust gas flow control system is configured to channel through the pressure control path exhaust gas not passing through the flow control path.

By channelling a first portion of the exhaust gas through the flow regulator and a second portion of the exhaust gas through the pressure regulator, the pressure regulator does not need to be dimensioned for the full exhaust gas flow. More precisely, the pressure regulator does not need to have a high accuracy over a wide flow rate range. In practice, the portion of exhaust gas flowing through the pressure regulator can be much less than would otherwise be the case if only a single pressure regulator were used to control the pressure.

As such, the flow conditions can be set to better match the operational range of the exhaust flow regulator and/or the exhaust gas pressure regulator. This, in turn, further improves the accuracy of the flow rate control and of the pressure level control.

In some embodiments, the exhaust gas flow control system is configured to maintain the flow rate through the flow control path at a predetermined exhaust gas flow rate.

In some embodiments, the exhaust gas flow control system comprises a monitoring arrangement to determine a flow value representative of the flow rate of the exhaust gas in the flow control path.

The monitoring arrangement may comprise a separate sensor that provides flow value readings independently of the operation of the exhaust flow regulator. The monitoring arrangement may comprise a configuration deriving the flow rate from operational parameters of the flow regulator. The monitoring arrangement may use both a separate sensor and a configuration to derive flow values from operational parameters, for instance to use operational parameters to continuously obtain readings and a separate sensor to verify the accuracy of the values derived from operational parameters.

In some embodiments, the exhaust gas flow control system comprises decision logic for determining a difference between a pre-determined flow rate and the flow value, and for issuing a control signal to compensate for the difference in order to maintain the flow rate through the flow control path at the pre-determined flow rate.

In some embodiments, the exhaust gas flow control system comprises a monitoring arrangement to determine a pressure value representative of the pressure rate through the pressure control path.

The monitoring arrangement may comprise a separate sensor that provides pressure value readings independently of the operation of the exhaust gas pressure regulator. The monitoring arrangement may comprise a configuration deriving the exhaust gas pressure value from operational parameters of the exhaust gas pressure regulator. The monitoring arrangement may use both a separate sensor and a configuration to derive pressure values from operational parameters, for instance to use operational parameters to continuously obtain readings and a separate sensor to verify the accuracy of the values derived from operational parameters.

For instance, a pressure sensor may be positioned at the exhaust port of the oxygenator.

In some embodiments, the exhaust gas flow control system comprises decision logic for determining a difference between a pre-determined pressure level and the pressure value, and for issuing a control signal to compensate for the difference in order to maintain the pressure in the pressure control path at the pre-determined pressure level.

Modulating the exhaust flow regulator and the exhaust gas pressure regulator in response to a flow value or pressure value, as determined by the monitoring arrangement, provides an interlock or feedback loop. These mechanisms provide a closed-loop control mechanism that is responsive to temporary fluctuations, to better maintain the flow rate and/or pressure level at their a pre-determined set points or as close as practically possible to the set point. The feedback loop allows a practically immediate adjustment to be made in order to maintain the flow rate and/or pressure level within a pre-determined range, or at a pre-determined level. This allows an immediate response to a change in oxygenation gas conditions without requiring an intervention by an operator.

In some embodiments, the exhaust gas flow control system is configured to use a common gas withdrawal arrangement for the flow control path and for the pressure control path.

This reduces the need for separate vacuum connectors. Particularly in a clinical environment, there may only be a fixed, limited number of vacuum connectors, and so the provision of a common gas withdrawal arrangement reduces the number of hospital vacuum connectors required for the ventilation system.

In some embodiments, the gas withdrawal arrangement comprises a low pressure source.

In some embodiments, the exhaust gas flow control system comprises a supply gas flow rate sensor configured to determine a supply gas flow value representative of the oxygenation gas flow rate supplied into the oxygenator, wherein the controller is configured to set the predetermined exhaust gas flow rate based on the supply gas flow value.

The supply gas flow rate sensor may be a gas flow sensor. The supply gas flow rate sensor may be provided in the form of an arrangement deriving the supply gas flow rate from flow parameters of an oxygenation gas supply module.

The ability to adjust the exhaust gas flow rate according to the supply gas flow rate facilitates the setting of steady state gas flow conditions inside the oxygenator.

By setting the exhaust gas flow rate based on the supply gas flow rate, the exhaust gas flow rate may be adjusted by the controller automatically in response to fluctuations in the supply gas flow rate. This facilitates the operation of the oxygenator.

In some embodiments, the controller is configured to maintain the predetermined exhaust gas flow rate at an offset value relative to supply gas flow rate.

This allows the exhaust gas flow rate to be set for instance at a fixed difference, or offset (higher or lower), relative to the supply gas flow rate.

In some embodiments, the offset value is set such that it does not exceed a flow capacity of the pressure regulator.

The offset can be set to a level corresponding to the preferred operating range of the pressure regulator. This allows the flow rate through the pressure regulator to be set as difference between exhaust gas channelled flow rate and supply gas flow rate. The offset can be set to a small level, which will allow the pressure regulator to be operated at a known, slow flow rate. This further increases the accuracy of the pressure regulator while allowing total exhaust flow rates much larger than would otherwise be feasible using known pressure regulators.

In some embodiments, the controller is configured to maintain the predetermined exhaust gas flow rate below the supply gas flow rate.

An exhaust gas flow rate below the supply gas flow rate allows a first portion of the exhaust gas to be flow-regulated by the exhaust gas flow regulator and a second portion of the exhaust gas to be controlled by the pressure regulator. As such, the pressure regulator does not need to be dimensioned for the full exhaust gas flow. In practice, the portion of exhaust gas flowing through the pressure regulator can be much less than would otherwise be the case. This allows pressure regulators with a smaller operational range to be used, which in practice facilities the provision of a pressure regulator with higher accuracy.

In practice, if the pre-determined pressure level is such that there is no inlet-to-exhaust pressure gradient, the pre-determined pressure level will be achieved by the exhaust gas pressure regulator at a flow rate that matches the supply gas flow rate. To achieve this, the exhaust gas pressure regulator needs to handle only the portion of gas not passing through the exhaust flow regulator.

Thereby, the invention allows large variations in exhaust flow rate to be controlled and to be maintained within tight tolerances. In particular, for sub-atmospheric oxygenation this allows sub-atmospheric pressure levels to be controlled and maintained within tight tolerances over a wide range of exhaust flow rates.

In some embodiments, the oxygenator comprises a pressure-relief mechanism to prevent over-pressurisation.

This allows the oxygenator to be operated as a closed system (ie, pressure isolated from atmospheric pressures) while also providing a pressure-relief functionality.

In accordance with a second aspect of the present invention, there is provided a method of controlling an exhaust gas flow rate for an oxygenator of an extracorporeal ventilation system as defined in claim 11.

The oxygenator is of the type comprising an oxygenation gas supply line and an exhaust line through which exhaust gas may be removed.

The method comprises the steps of: providing a controller, providing a flow control path, providing a pressure control path, providing an exhaust flow regulator responsive to the controller, providing an exhaust gas pressure regulator responsive to the controller, and using the controller to operate the exhaust gas pressure regulator to modulate the exhaust gas pressure, thereby to maintain a pre-determined pressure level in the exhaust line, and controlling the flow rate in the flow control path using the exhaust flow regulator, and controlling the pressure at the pressure control path using the exhaust gas pressure regulator.

The second aspect relates to methods of using embodiments of the first aspect in order to be able to maintain a predetermined pressure level in the exhaust line of an oxygenator, in the context of providing a predetermined pressure-profile from the inlet to the exhaust of an oxygenator.

In some embodiments, the method comprises providing a supply line pressure regulator upstream of the oxygenator.

In some embodiments, the method comprises providing an exhaust gas pressure regulator configured to operate at sub-atmospheric pressure and operating the exhaust gas pressure regulator to maintain a sub-atmospheric pressure level in the exhaust line.

In some embodiments, the method comprises, using the controller, operating the exhaust flow regulator to modulate the exhaust flow rate, thereby to maintain a pre-determined flow rate of the exhaust gas passing through the exhaust flow regulator.

In some embodiments, the method comprises channelling through the pressure control path exhaust gas not passing through the flow control path.

In some embodiments, the method comprises maintaining the flow rate through the flow control path at the predetermined exhaust gas flow rate.

In some embodiments, the method comprises using a monitoring arrangement to determine a flow value representative of the flow rate of the exhaust gas in the flow control path.

In some embodiments, the method comprises using decision logic for determining a difference between a pre-determined flow rate and the flow value, and for issuing a control signal to compensate for the difference in order to maintain the flow rate through the flow control path at the pre-determined flow rate.

In some embodiments, the method comprises using a monitoring arrangement to determine a pressure value representative of the pressure in the pressure control path.

In some embodiments, the method comprises using decision logic for determining a difference between a pre-determined pressure level and the pressure value, and for issuing a control signal to compensate for the difference in order to maintain the pressure in the pressure control path at the pre-determined pressure level.

In some embodiments, the method comprises providing a common gas withdrawal arrangement for the flow control path and for the pressure control path.

In some embodiments, the method comprises providing a low pressure source for use with the gas withdrawal arrangement.

In some embodiments, the method comprises providing a supply gas flow rate sensor configured to determine a supply gas flow value representative of the oxygenation gas flow rate supplied into the oxygenator, and using the controller to set the predetermined exhaust gas flow rate based on the supply gas flow value.

In some embodiments, the method comprises using the controller to maintain the predetermined exhaust gas flow rate at an offset value relative to supply gas flow rate.

In some embodiments, the method comprises setting the offset value to a level not exceeding a flow capacity of the pressure regulator.

In some embodiments, the method comprises using the controller to maintain the predetermined exhaust gas flow rate at a level below the supply gas flow rate.

In some embodiments, the method comprises providing the oxygenator with a pressure-relief mechanism to prevent over-pressurisation.

The embodiments of the first and second aspects are thought to facilitate the provision of defined hypobaric oxygenation conditions, in particular exhaust flow rate and exhaust gas pressure levels, over prolonged periods of time.

To set out a context for the benefits of hypobaric (sub-atmospheric) ventilation, a summary of relevant mechanism taking place during routine atmospheric oxygenation is provided, using the example of a hollow fibre oxygenator. Oxygenation gas (ie gas that is similar to air and mixed to a required oxygen and nitrogen content in order to achieve a desired partial pressure of oxygen and partial pressure of carbon dioxide in the arterial blood) is directed via a tube and, if required, also through an anaesthetic agent vaporizer, to the gas inlet of the oxygenator, and through the bundle of hollow fibres (the gas phase), while blood is passed inside the oxygenator over the outside (the blood phase) of the hollow fibres. The fibre walls are gas-permeable and gas transfer occurs via the fibre walls due to the diffusion gradient from higher concentration (e.g., of oxygen in the oxygenation gas, or of carbon dioxide in the venous blood) to lower concentration (e.g., of oxygen in the venous blood, or of carbon dioxide in the oxygenation gas).

The blood exiting the oxygenator is referred to as arterial blood and is oxygenated to have a required partial pressure of oxygen in the arterial blood (PaO2) and a required partial pressure of carbon dioxide in the arterial blood (PaCO2). PaO2 and PaCO2 are adjusted as follows. PaO2 can be influenced by adjusting by the oxygen content of the oxygenation gas (Fraction of Inspired Oxygen, FiO2), relative to the fraction of nitrogen in the oxygenation gas (FiN2). Most of the blended air consists of nitrogen. PaCO2 can be influenced by adjusting the flow rate (commonly referred to as "Sweep") of the oxygenation gas. Nitrogen in the gas phase seeks to balance itself to be equal in pressure in the gas phase compared to the blood phase.

A problem with extracorporeal oxygenation systems exists with the risk of formation of gaseous microemboli bubbles (GME) which may be propelled through the blood into the circulatory system, especially when the GME bubble has a high nitrogen content. Nitrogen-containing GME are produced when air comes into contact with blood. There are many opportunities for this to happen in a clinical scenario, e.g., when air and blood mix during blood suction, in open cardiac chambers, during certain drug administration procedures, during high negative pressure areas in the pump circuit, or during warming when the temperature of the blood does not allow the current volume of nitrogen to stay dissolved in solution (and nitrogen thereby "comes out of solution" in the form of bubbles).

Once in the blood stream, there often is little to no diffusion gradient between a nitrogen-containing bubble in the body and surrounding blood/tissues. Thus, a nitrogen-containing bubble, once present, tends not to dissolve into solution. GME in the blood cause proteins to stick to the bubble surfaces and relatively quickly develop a coating, which acts as a barrier further inhibiting diffusion of gases into/out of the bubble. This nitrogen-containing, protein-coated bubble then behaves much like a hollow particle with a solid surface, with the same potential morbidities associated with it as are associated with solid embolus obstruction of blood flow to the tissues. Additionally, GME can harm intimal vessel layers, leading to blood vessel inflammation. This also stimulates the coagulation pathways, which can lead to bleeding/clotting problems.

Attempts to decrease GME during extracorporeal ventilation include several techniques, such as limiting blood temperature differentials, minimizing blood suction return directly to the circuit, operating any drug injection into the blood at slow rates, flooding the operative field with CO2, utilization of de-foaming chemicals in the venous/cardiotomy filters/reservoir, and arterial bubble trap/purge devices. Despite these attempts, presence of GME, as measured by sensitive instruments, is a common event in the arterial blood in extracorporeal systems.

As set out above, nitrogen is used in the oxygenation gas to set the partial pressure of oxygen in the oxygenation gas (FiO2), which, in turn, directly influences the partial pressure of oxygen in the arterial blood (PaO2) exiting the oxygenator.

By reducing or eliminating nitrogen in the oxygenation gas, e.g., by using pure oxygen (or a mix of oxygen and carbon dioxide), the partial pressure of nitrogen in the blood can be greatly decreased, even to the point of practical elimination. To illustrate this with an example, instead of an oxygen content similar to air, in the region of 20 to 21% (the remaining 79 to 80% being mostly nitrogen), the oxygen content may be close to 100% (with negligible nitrogen content) in the oxygenation gas entering the inlet of the oxygenator. However, if 100% oxygen is used at atmospheric pressure for extracorporeal blood ventilation, this will result in a very high partial pressure of oxygen in the arterial blood (PaO2). A high PaO2 is undesirable because it has adverse effects on a patient, e.g., due to damaging free oxygen radicals that can be produced. Furthermore, high partial pressures of gases in blood have the counterproductive effect of increasing the tendency for GME development due to the dissolution-inhibiting effect.

However, if higher oxygen content is provided at sub-atmospheric pressures, the corresponding partial pressure in the arterial blood leads to a lower oxygen content in the blood at equilibrium. As such, at sub-atmospheric pressure levels, a non-gas-saturated arterial blood environment is provided in the oxygenator, and the partial pressure of oxygen PaO2 is lower without the need to use nitrogen in the oxygenation gas.

Furthermore, in the non-gas-saturated condition, any bubbles in the blood tend to dissolve more quickly, practically before a protein coating can form on the bubble-blood interface. There is therefore believed to be a two-fold benefit of avoiding the need for nitrogen in the oxygenation gas and hypobaric ventilation: in addition to preventing GME formation, non-gas-saturated blood is also believed to promote the dissolution of existing bubbles.

The provision of an exhaust gas flow control system facilitates maintaining gas flow rates within narrow margins, particularly at sub-atmospheric pressure levels that are also maintained within narrow margins. This is of interest during hypobaric ventilation, which is an oxygenation procedure at sub-atmospheric pressures.

BRIEF DESCRIPTION OF THE DRAWINGS

Exemplary embodiments of the invention will now be described with reference to the Figures, in which.

DETAILED DESCRIPTION OF SPECIFIC EMBODIMENTS

Figure 1:
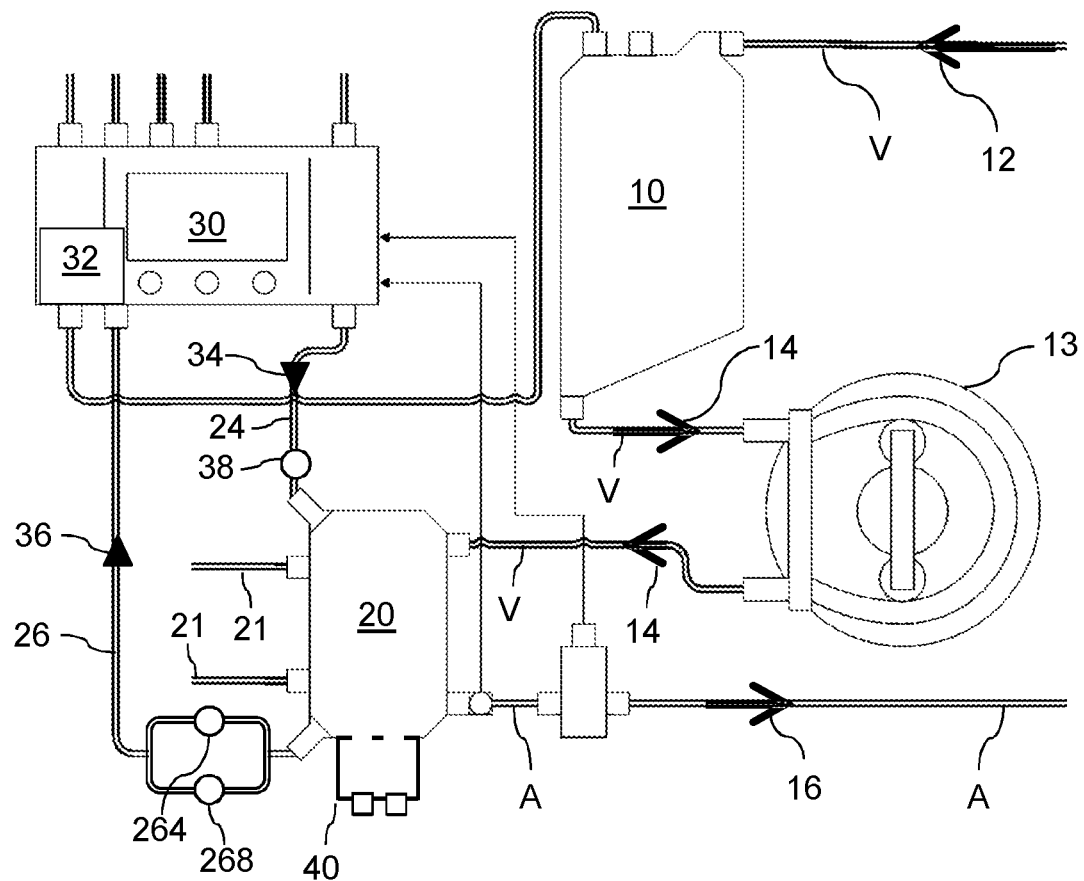
FIG. 1 shows a schematic arrangement of an oxygenation system incorporating an exemplary embodiment of the invention.

FIG. 1 shows, schematically, components of a ventilation system. The ventilation system comprises a venous line 12 provided to receive venous blood V from a patient into a venous reservoir 10. From the venous reservoir 10, the blood is drawn by a pump 13 via a main line 14 and pumped towards an oxygenator 20 in which the venous blood V is exposed to an oxygenation gas to be oxygenated and for its carbon dioxide levels to be adjusted. The oxygenated blood exits, as arterial blood A, the oxygenator 20 via an outlet line 16 from where it may be provided to a patient.

FIG. 1 also shows a gas blender 30 in which oxygenation gas is prepared (mixed and brought to appropriate flow conditions such as flow rate and pressure) to be provided via an oxygenation gas supply line 24 in a direction indicated by the arrow 34 into the oxygenator inlet for exposure to blood in the oxygenator. For instance, this may a blender 30 as described in International patent application WO2016/087859 by the present applicant. The oxygenation gas is withdrawn by use of a withdrawal system 32 (e.g., vacuum-assisted suction) from the oxygenator 20 via an exhaust line 26 in the direction indicated by the arrow 36. The exhaust line 26 comprises two gas flow path ways that will be described in more detail with reference to FIG. 3 below. One gas flow path way comprises a flow controller 264. The other gas flow path way comprises a pressure regulator 268.

The temperature in the oxygenator 20 is controlled using temperature-control water via water supply lines 21.

The oxygenation gas supply line 24 comprises a vacuum regulator valve 38 constituting a pressure regulator upstream of the oxygenator 20. By way of the vacuum regulator valve 38, atmospheric pressure may be maintained upstream of the vacuum regulator valve 38 in the oxygenation gas supply line 24, and sub-atmospheric pressure may be established downstream of the vacuum regulator valve 38, and therefore in the oxygenator 20.

This allows gas to be processed at atmospheric pressures upstream of the vacuum regulator valve 38. For instance, an anaesthesia vaporiser (not shown in FIG. 1) may be provided to release anaesthetic agent into the oxygenation gas supply. If the anaesthesia vaporiser is exposed to sub-atmospheric pressures, the anaesthetic agent would evaporate at a much higher rate, with undesirable side effects. The provision of a vacuum regulator valve 38 downstream of an anaesthesia vaporiser allows hypobaric oxygenation to be performed on systems utilising anaesthetic agent in the oxygenation gas.

In the arrangement of FIG. 1 there is also depicted a cap 40 installed on the oxygenator 20. The cap 40 constitutes a pressure-isolating component. The cap 40 comprises a pressure-relief mechanism as a fail-safe mechanism to avoid over-pressurisation in the oxygenator. For the purposes of the present application, the oxygenator 20 can be operated as a closed system, ie as a system that is pressure-isolated from ambient pressure conditions. As such, the oxygenator 20 is equipped for hypobaric oxygenation. The mechanism of the cap 40 includes pressure-relief valves (e.g., one or more duckbill valves) that activate passively when the pressure in the oxygenator exhaust chamber reaches atmospheric pressure. The cap 40 provides a fail-safe mechanism against over-pressurisation. Without a fail-safe mechanism, over-pressurisation may occur if a gas line is blocked e.g., by a member of staff accidentally bending a line. The fail-safe mechanism is described in more detail in the co-pending Great British patent application GB1705556.7. For the purposes of this specification, the oxygenator 20 can be operated in a closed-system mode and the pressure profile from supply gas inlet to exhaust can be influenced by controlling the pressure upstream and downstream of the oxygenator 20, e.g., by use of the vacuum regulator valve 38 and the pressure regulator 268. As a more general statement, the oxygenator 20 comprises a configuration permitting it to be operated in a manner pressure-isolated from atmospheric pressure and comprises a fail-safe mechanism against over-pressurisation.

Figure 2:
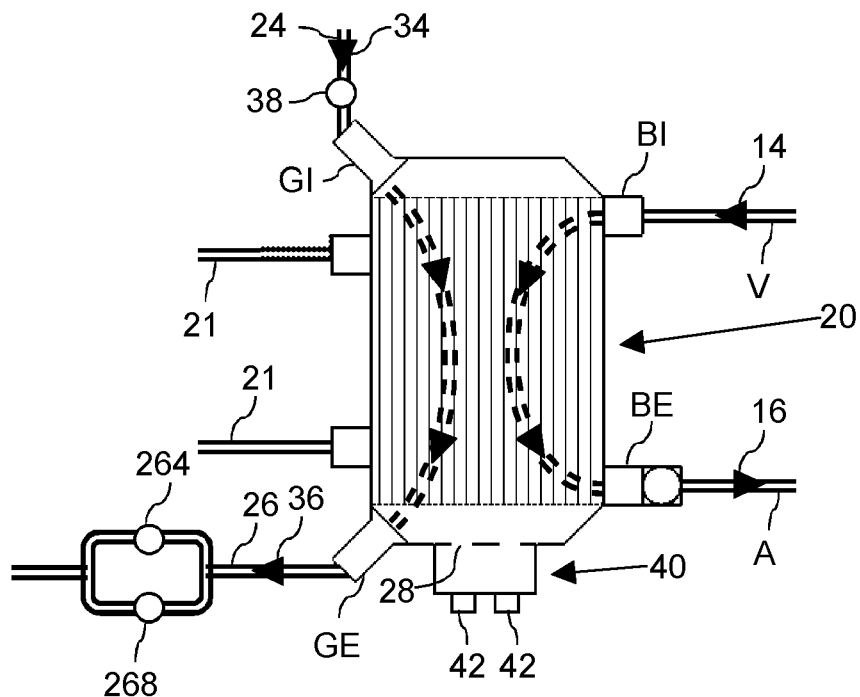
FIG. 2 shows a schematic arrangement of an oxygenator comprising an exemplary embodiment of the invention.

FIG. 2 shows in more detail a schematic drawing of the oxygenator 20 together with the cap 40. For ease of reference, the same numerals are used in FIG. 2 as in FIG. 1 for corresponding components. FIG. 2 shows the main line 14 for supply of venous blood V into the oxygenator via a blood inlet BI, from where blood is passed via a gas-permeable gas-blood interface at which the venous blood V is exposed to the oxygenation gas. For instance, the gas-permeable interface may be provided across gas-permeable walls of hollow-fibre bundles. In an oxygenated condition, the blood exits as arterial blood A via a blood outlet BE into the outlet line 16. The oxygenation gas enters the oxygenator 20 via the gas inlet GI and is transported along the gas-permeable interface and withdrawn via the gas exit GE. The gas exit GE constitutes a main exhaust port via the exhaust line 26, and is configured to permit a controlled removal (e.g., removal at a controlled flow rate) of exhaust gas.

In addition to the main exhaust port constituted by the gas exit GE, the housing 22 comprises a plurality of openings 28 constituting auxiliary exhausts which provide a gas passage between the inside of the oxygenator and the outside. By virtue of the openings 28, the oxygenator 20 may be referred to as a 'porous', or 'leaky', oxygenator type. In particular, although indicated only schematically, in operation all ports or connections with the oxygenator 20, such as the blood inlet BI, the blood outlet BE, the gas inlet GI, the gas exit GE, and the water supply lines 21, are not open to atmospheric pressures and do not permit pressure-equilibration between the inside of the oxygenator and its outside. Thus, when the oxygenator is connected and in use, apart from the openings 28 there are no other gas passages across the housing 22 from the inside to the outside of the oxygenator 20.

As shown in FIG. 2, the oxygenator 20 is provided with a cap 40 constituting a pressure-isolating arrangement. The cap 40 is positioned over the openings 28 and comprises a plurality of integral duckbill valves 42. Each duckbill valve 42 constitutes a pressure-relief unit of a pressure-relief arrangement. The duckbill valves 42 are configured as positive pressure-relief valves activating at a pressure-relief threshold, which may be an atmospheric pressure level.

The cap 40 is attached to the oxygenator 20 in a manner that permits gas passage between the inside of the oxygenator and the outside via the openings 28 when the duckbill valves 42 open, i.e., when the pressure inside the oxygenator chamber exceeds the pressure-relief threshold of the duckbill valves 42. Thus, the cap 40 can be used to maintain a closed system unless the pressure in the oxygenator exhaust chamber increases to atmospheric pressure, at which point the duckbill valves 42 passively activate to provide the pressure-relief function.

Figure 3:
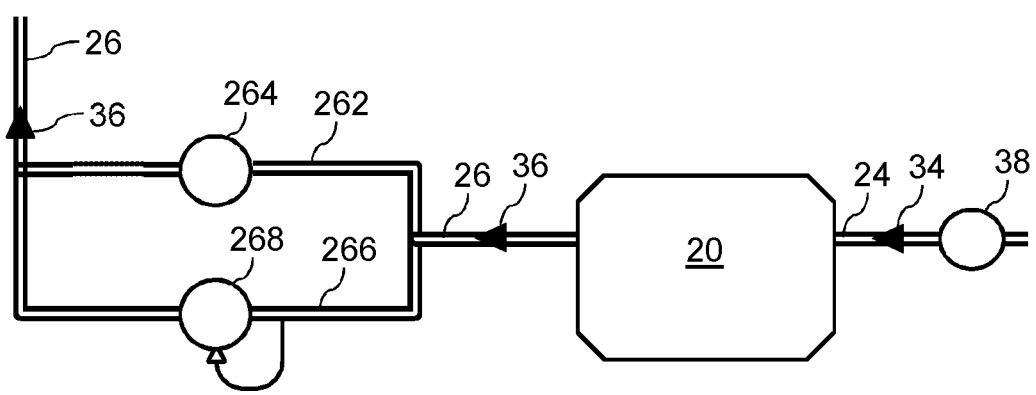
FIG. 3 shows a schematic illustration relating to an exemplary embodiment of the invention.

Turning to FIG. 3, for ease of reference, the same numerals are used in FIG. 3 as in FIGS. 1 and 2 for corresponding components. FIG. 3 shows the gas supply line 24 with the vacuum regulator valve 38 supplying the oxygenator 20 and the exhaust line 26 comprising a first gas flow path 262 in which the flow controller 264 is provided and a second gas flow path 266 in which the pressure regulator 268 is provided. The vacuum regulator valve 38, the flow controller 264, and the pressure regulator 268 are each controlled by a control system (not shown) and allow the flow rate and pressure conditions from the gas supply inlet to the exhaust side of the oxygenator 20 to be modulated.

As depicted in FIG. 3, the first gas flow path 262 and the second gas flow path 266 join into a common exhaust line 26 prior to their connection to a vacuum source. The flow controller 264 and the pressure regulator 268 may be integrated with the withdrawal system 32, and the withdrawal system 32 may be integrated with the gas blender 30 into a single gas management device. The first gas flow path 262 and the second gas flow path 266 may be connected to the withdrawal system 32 by separate lines. Although not shown in FIG. 3, a single device may be used in a single exhaust line 26 to provide both a flow control function and a pressure regulation function.

The oxygenator 20 may operate in an atmospheric mode or in a sub-atmospheric mode. In the sub-atmospheric mode, the oxygenator is pressure-isolated such that the chamber inside the oxygenator 20 can be considered to be a closed system. The pressure isolation may be achieved by way of the cap 40.

Oxygenation gas is supplied to the oxygenator 20 via the supply line 24, and the withdrawal system 32 (see FIG. 21) is used to remove exhaust gas via the exhaust line 26. The flow controller 264 is used to transport a portion of the exhaust gas via the first gas flow path 262. The remainder of the exhaust gas is channelled via the second gas flow path 266 and passes the pressure regulator 268.

The flow regulator may be set to a flow rate at an offset value below the supply gas flow rate. The supply gas flow rate may be known from operational parameters or from a supply gas flow sensor.

To illustrate the concept with exemplary numerical values, the supply gas may enter the oxygenator 20 at a rate of 4 litres per minute (lpm) and at a pressure of 500 mbar downstream of the vacuum regulator valve 38. The supply gas flow rate may be determined by a supply gas flow sensor, or from operational parameters provided by the gas blender 30 or vacuum pressure regulator 38. Maintaining a pressure of 500 mbar from the inlet GI to the exhaust GE across the oxygenator is greatly facilitated if it can be ensured that the exhaust gas is removed at a similar flow rate and pressure, i.e., at 4 lpm at 500 mbar.

Conventionally, it would be challenging to provide a pressure regulator operating at 4 lpm at 500 mbar that is also able to modulate with high accuracy in the 4 lpm region, for example +/−1.5 lpm. This is because in order to achieve a modulation of practically 4 lpm+/−1.5 lpm it would require a pressure regulator modulating with high accuracy in a range from 2.5 lpm to 5.5 lpm.

By way of the depicted arrangement, the offset value may be set to 1.5 lpm. The offset value may be chosen such that the operational range of the pressure regulator 268 provides for practical purposes a range with 'negative' values. E.g. the pressure regulator 268 with an operational range of 0 to 3 lpm, added to a flow rate of 2.5 lpm, provides a system operating from 2.5 lpm+0 lpm to 2.5 lpm+3 lpm, and so practically at a range of 4 lpm+/−1.5 lpm with the accuracy of a pressure regulator with an operational range of 0 to 3 lpm. A pressure regulator with sufficient accuracy in the 0 to 3 lpm range may be easier to source than a pressure regulator operating with the same level of accuracy in a range of up to 5.5 lpm. Other suitable offset values may be chosen.

In the present example, the flow rate to be channelled via the first gas flow path 262 is calculated as 2.5 lpm (4 lpm supply gas flow rate−1.5 lpm offset value), which is the pre-determined exhaust gas flow rate to be maintained by the flow controller 264. The controller thus operates the flow controller 264 to flow exhaust gas through the first flow path 262 at a flow rate of 2.5 lpm. In order to match the removed amount exhaust gas to the supply gas, a remaining offset of 1.5 lpm are to be removed at the exhaust side. By way of the withdrawal system 32, the remaining 1.5 lpm constitute an offset that is channelled via the second gas flow path 266 and, thus, via the pressure regulator 268 which is operating within is operational range of 0 to 3 lpm, and so the remaining 1.5 lpm sit right within the operational range. This facilitates modulating the pressure to a pre-determined set point of 500 mbar with great accuracy. It will be understood that the pressure is electronically variable up to any suitable value, such as e.g., 500 mbar below atmospheric pressure.

If the total (oxygenation gas and exhaust gas) flow rates are increased, for example from 4 lpm to 7 lpm, the offset remains the same 1.5 lpm. 5.5 lpm (7 lpm−1.5 lpm) are channelled via the flow controller 264 and the remaining 1.5 lpm via the pressure regulator 268 for pressure regulation. The pressure regulator can continue to operate in its operational range between 0 to 3 lpm practically independently of the change of the total gas flow rate.

Note that in the described setup, the pre-determined exhaust gas flow rate is not the total exhaust gas flow rate, but the portion of exhaust gas passing via the exhaust gas flow regulator. The flow rate in the first flow path 232 downstream of the flow regulator 264 may thus be less than the supply gas flow rate of 4 lpm, as excess gas may be vented (excess gas venting not shown in the Figures). However, the pressure of 500 mbar in the exhaust line 26 will be achieved by the pressure regulator 268 when the flow rate via the exhaust GE closely matches the supply gas flow rate. Thereby it is achieved that the exhaust gas withdrawn from the oxygenator 20, at the exhaust GE, corresponds to the supply gas flow rate.

Thereby, the flow rate and the pressure level at the exhaust side are modulated to the required levels with high accuracy.

Using a flow controller alone, it would be more challenging to maintain a sub-atmospheric pressure level at a pre-determined level. The above arrangement greatly facilitates the ability to maintain a pre-determined pressure level at the exhaust side of the oxygenator.

Figure 4:
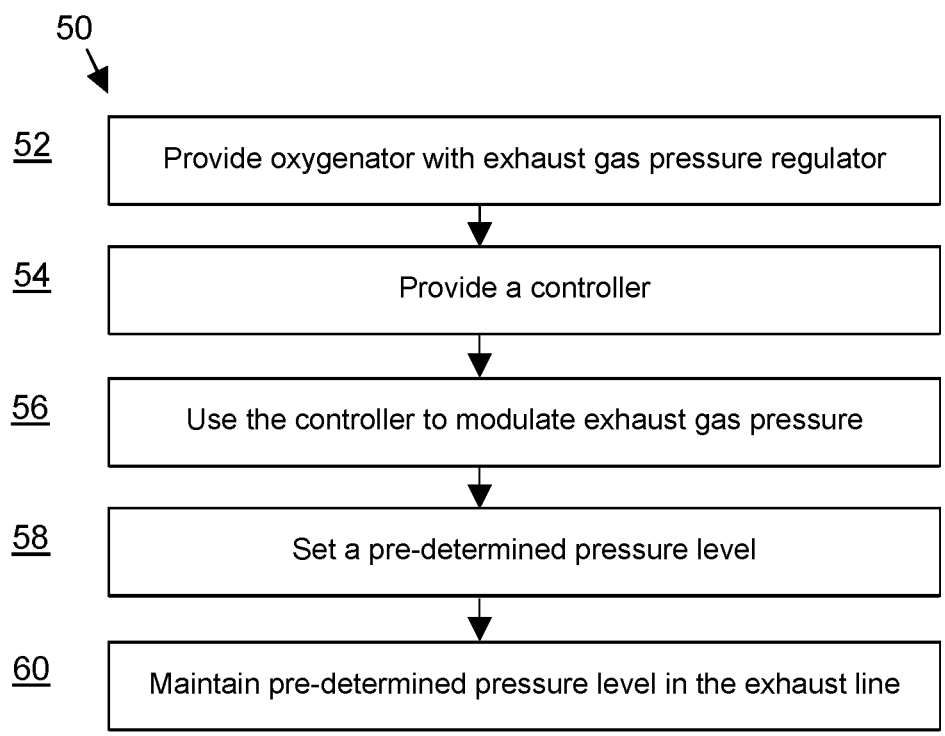
FIG. 4 shows exemplary steps of a method embodying the invention.

FIG. 4 shows exemplary steps of a method 50 of controlling an exhaust gas flow rate for an oxygenator of an extracorporeal ventilation system. The oxygenator is of a type comprising an oxygenation gas supply line and an exhaust line through which exhaust gas may be removed. The method 50 comprises a step 52 of providing the oxygenator with an exhaust gas pressure regulator. In step 54, a controller is provided. In step 56, the controller is used to modulate the exhaust gas pressure by controlling the exhaust gas pressure regulator. In step 58, a pre-determined pressure level is set. For instance, the pre-determined pressure level may be 500 mbar below atmospheric pressure. In step 60, the controller is used to maintain the pre-determined pressure level in the exhaust line.

What is claimed is:

1. An exhaust gas flow control system provided for an oxygenator of an extracorporeal ventilation system, wherein the oxygenator is of a type connected to an oxygenation gas supply line and to an exhaust line through which exhaust gas may be removed, the exhaust gas flow control system comprising:
    a flow control path,
    a pressure control path,
    an exhaust flow regulator responsive to a controller, and
    an exhaust gas pressure regulator responsive to the controller configured to maintain a pre-determined pressure level in the exhaust line,
    wherein the flow control path is controlled by the exhaust flow regulator and the pressure control path is controlled by the exhaust gas pressure regulator,
    wherein the controller is configured to maintain a pre-determined flow rate of the exhaust gas passing through the exhaust flow regulator, and
    wherein the exhaust gas flow control system is configured to channel through the pressure control path exhaust gas not passing through the flow control path.

2. The exhaust gas flow control system according to claim 1, comprising a supply line pressure regulator upstream of the oxygenator.

3. The exhaust gas flow control system according to claim 1, wherein the exhaust gas pressure regulator is configured to maintain a sub-atmospheric pressure level in the exhaust line.

4. The exhaust gas flow control system according to claim 1, configured to maintain the flow rate through the flow control path at the predetermined exhaust gas flow rate.

5. The exhaust gas flow control system according to claim 1, comprising a monitoring arrangement to determine a flow value representative of the flow rate of the exhaust gas in the flow control path, and comprising decision logic for determining a difference between a pre-determined flow rate and the flow value, and for issuing a control signal to compensate for the difference in order to maintain the flow rate through the flow control path at the pre-determined flow rate.

6. The exhaust gas flow control system according to claim 1, comprising a monitoring arrangement to determine a pressure value representative of the pressure in the pressure control path, and comprising decision logic for determining a difference between a pre-determined pressure level and the pressure value, and for issuing a control signal to compensate for the difference in order to maintain the pressure in the pressure control path at the pre-determined pressure level.

7. The exhaust gas flow control system according to claim 1, comprising a supply gas flow rate sensor configured to determine a supply gas flow value representative of the oxygenation gas flow rate supplied into the oxygenator, wherein the controller is configured to set the predetermined exhaust gas flow rate based on the supply gas flow value.

8. The exhaust gas flow control system according to claim 7, wherein the controller is configured to maintain the predetermined exhaust gas flow rate at an offset value relative to supply gas flow rate.

9. A method of controlling an exhaust gas flow rate for an oxygenator of an extracorporeal ventilation system, wherein the oxygenator is of a type comprising an oxygenation gas supply line and an exhaust line through which exhaust gas may be removed, the method comprising:
 providing a controller,
 providing a flow control path,
 providing a pressure control path,
 providing an exhaust flow regulator responsive to the controller,
 providing an exhaust gas pressure regulator responsive to the controller, and
 using the controller, operating the exhaust gas pressure regulator to modulate the exhaust gas pressure, thereby to maintain a pre-determined pressure level in the exhaust line,
 controlling the flow rate in the flow control path using the exhaust flow regulator,
 controlling the pressure at the pressure control path using the exhaust gas pressure regulator, and
 channelling through the pressure control path exhaust gas not passing through the flow control path.

10. The method according to claim 9, comprising providing a supply line pressure regulator upstream of the oxygenator.

11. The method according to claim 9, comprising providing an exhaust gas pressure regulator configured to operate at sub-atmospheric pressure and operating the exhaust gas pressure regulator to maintain a sub-atmospheric pressure level in the exhaust line.

12. The method according to claim 11, comprising, using the controller, operating the exhaust flow regulator to modulate the exhaust flow rate, thereby to maintain a pre-determined flow rate of the exhaust gas passing through the exhaust flow regulator.

13. The method according to claim 9, comprising maintaining the flow rate through the flow control path at the predetermined exhaust gas flow rate.

14. The method according to claim 9, comprising providing a common gas withdrawal arrangement for the flow control path and for the pressure control path.

15. The method according to claim 9, comprising providing a supply gas flow rate sensor configured to determine a supply gas flow value representative of the oxygenation gas flow rate supplied into the oxygenator, and using the controller to set the predetermined exhaust gas flow rate based on the supply gas flow value, thereby providing a configuration capable of using the controller to maintain the predetermined exhaust gas flow rate at an offset value relative to supply gas flow rate.

16. The method according to claim 15, comprising setting the offset value to a level not exceeding a flow capacity of the pressure regulator.

17. The method according to claim 15, comprising using the controller to maintain the predetermined exhaust gas flow rate at a level below the supply gas flow rate.

* * * * *